United States Patent [19]
Postlethwaite et al.

[11] Patent Number: 6,088,424
[45] Date of Patent: Jul. 11, 2000

[54] APPARATUS AND METHOD FOR PRODUCING A PICTURE-IN-A-PICTURE MOTION X-RAY IMAGE

[75] Inventors: John R. Postlethwaite; Steve J. Robbins, both of Palm Harbor, Fla.

[73] Assignee: VF Works, Inc., Palm Harbor, Fla.

[21] Appl. No.: 09/158,960

[22] Filed: Sep. 22, 1998

[51] Int. Cl.[7] .................................................. G01N 23/04
[52] U.S. Cl. ........................... 378/63; 378/98.2; 378/197
[58] Field of Search .............................. 378/62, 63, 98.2, 378/193, 197; 348/564, 565

[56] References Cited

U.S. PATENT DOCUMENTS

| | | | |
|---|---|---|---|
| 4,920,413 | 4/1990 | Nakamura et al. | 348/74 |
| 5,077,769 | 12/1991 | Franciose | 378/99 |
| 5,519,754 | 5/1996 | Postlethwaite | 378/197 |
| 6,007,243 | 12/1999 | Ergun et al. | 378/197 |

*Primary Examiner*—David P. Porta
*Assistant Examiner*—Allen C Ho
*Attorney, Agent, or Firm*—Larson & Larson, P.A.; James E. Larson

[57] ABSTRACT

A videofluoroscopy device having a rotatable and vertically moveable c-arm, with an x-ray device mounted thereupon, is connected to a system for producing a picture-in-a-picture (PIP) real time motion x-ray image. A video camera mounted on the videofluoroscopy device c-arm, proximal to the x-ray device, permits an operator to view an external picture of the patient while simultaneously viewing the x-ray image. An electrical circuit coupled to the system converts the two video signals into one PIP image. The single PIP image can be recorded on video tape and/or viewed on a monitor. In the preferred embodiment, the "full-screen" image is the motion z-ray image while the overlaid smaller image, placed in a box in the corner of the video frame, is that of an external view of the patient corresponding to the portion of the body being x-rayed.

20 Claims, 5 Drawing Sheets

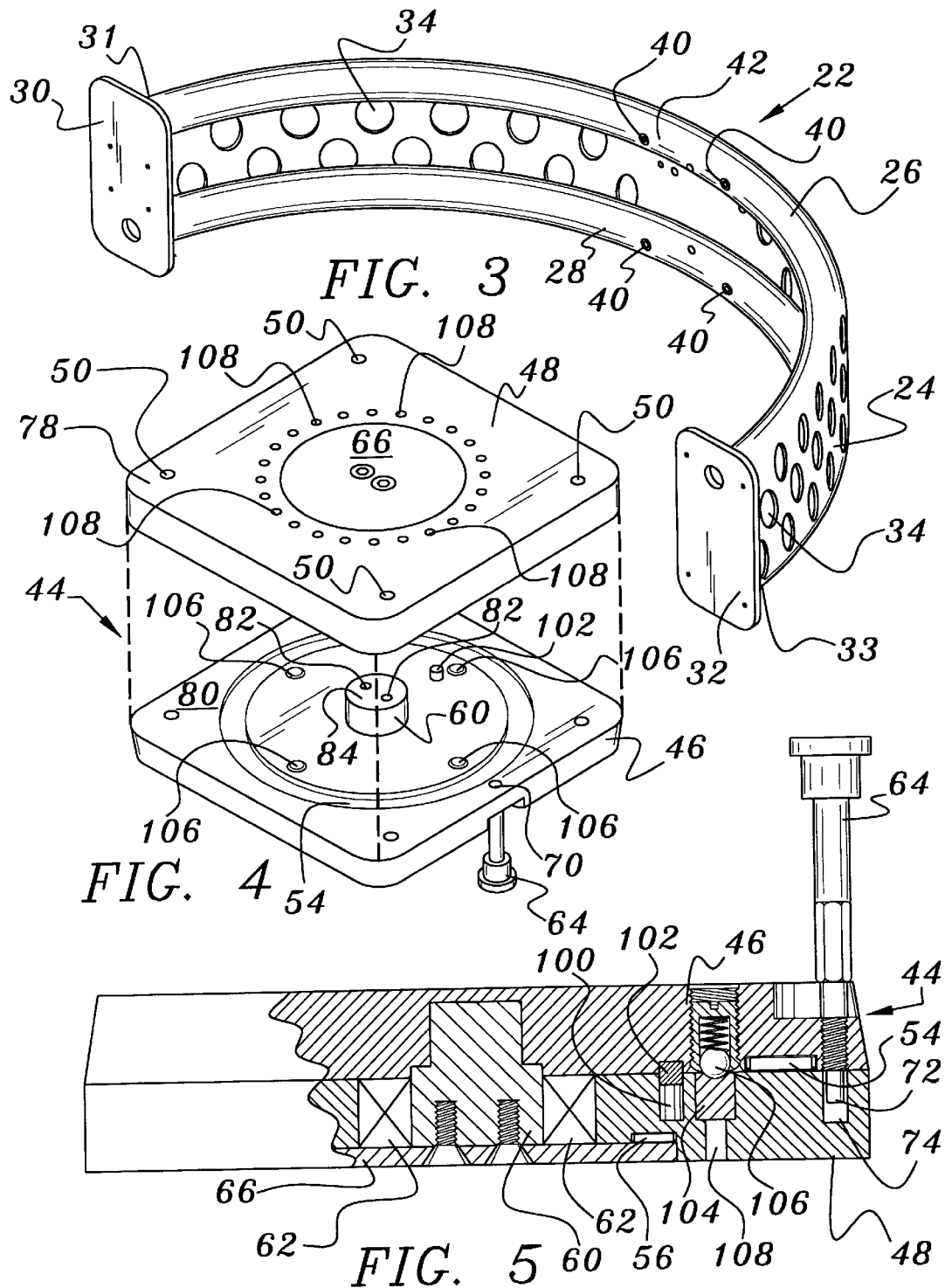

APPARATUS AND METHOD FOR PRODUCING A PICTURE-IN-A-PICTURE MOTION X-RAY IMAGE

BACKGROUND OF THE INVENTION

1. Field of the Invention

The present invention relates to a videofluoroscopy device. More particularly, it relates to a videofluoroscopy system capable of producing a picture-in-a-picture motion x-ray image.

2. Background of the Prior Art

Videofluoroscopy devices are known in the prior art and are most commonly used by doctors and practitioners in the fields of chiropractic, orthopedic, osteopathic and sports medicine. The videofluoroscopy device allows a doctor or practitioner to assess problems or abnormalities of a patient's joints, muscles or bones by recording a real time x-ray image of such joints, muscles, and bones on video tape. The video tape can be reviewed at the doctor's or practitioner's leisure, allowing for careful and precise evaluation of a particular problem which might not be evident from an external exam or from conventional static x-ray photos.

Most videofluoroscopy devices are relatively small in design and mount to a wall. The device may be used in an office setting or in a mobile medical vehicle. The videofluoroscopy device mainly consists of a vertical housing enclosing a movement mechanism, the movement mechanism operating a c-arm, the c-arm mounted perpendicularly to a longitudinal axis of the vertical housing and supporting an x-ray device.

The movement mechanism directs the c-arm upward and downward along the longitudinal axis of the vertical housing. The x-ray device supported upon the c-arm transmits a real time x-ray image to a video tape recorder thereby recording the movement of the entire body of a patient. In particular, the device records x-ray images of the joints, muscles, and bones and their corresponding movements.

Although videofluoroscopy devices and systems of the prior art have been successful in rending real time x-ray images of individuals, none permit the x-ray viewer to simultaneously view the real time x-ray and an external real time image of the patient. A need exists for doctors and others to simultaneously view the real time x-ray with an external real time image of a patient. Such a system and method would permit practitioners to see the correlation between the external and internal movement of related joints, muscles and bones of a patient. A novel system and method that incorporates picture-in-a-picture (PIP) technology could be used to solve this problem.

SUMMARY OF THE INVENTION

The present invention discloses a system and method for producing a real time or motion x-ray image which has a corresponding external real time or motion image of the patient laid thereover; a so called "picture-in-a-picture" (PIP) motion x-ray image. PIP technology, most often used with televisions, allows a viewer to watch a first program "full-screen" while monitoring a second program in a smaller box in the corner of the full-screen image.

The system of the present invention includes a videofluoroscopy device having an x-ray image producing device and a video camera mounted upon an arcuate shaped c-arm which is moveable and rotatable along a longitudinal axis of the videofluoroscopy device. Coupled to the x-ray image device and the video camera is an electrical circuit capable of combining the two images into a PIP image. Coupled to the electrical circuit are a video tape recorder and a video monitor for recording and monitoring, respectively, the novel PIP motion x-ray image.

BRIEF DESCRIPTION OF THE DRAWINGS

FIG. 3 is a perspective view of the c-arm;

FIG. 4 is a perspective view, partially exploded, of the rotation means;

FIG. 5 is a side elevational view, partially in-section, of the rotation means;

DETAILED DESCRIPTION OF THE PREFERRED EMBODIMENTS

Figure 1:
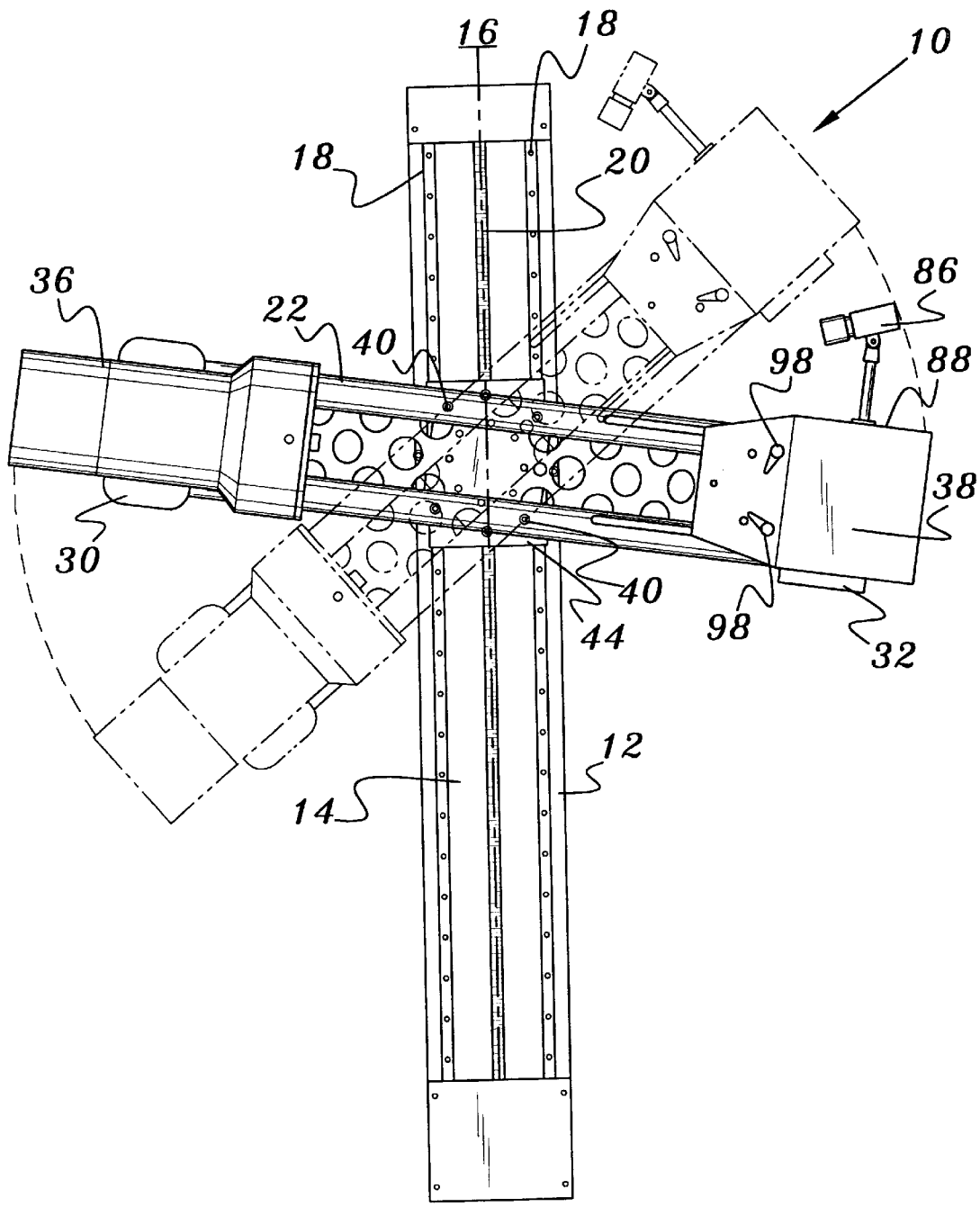
FIG. 1 is a front elevational view of a videofluoroscopy device used in the system and method of the present invention.

Referring to FIG. 1, a videofluoroscopy device 10 is shown having a vertical housing 12 defining a vertical channel 14 along a vertical axis 16. Mounted within vertical channel 14 are a pair of guide rails 18 and a center worm screw 20. Guide rails 18 and worm screw 20 work in conjunction to permit an arcuate shaped c-arm 22 (see FIG. 3) to move along vertical axis 16. The means for mounting and the function of guide rails 18 and worm screw 20 and the function of a motor (not shown) is disclosed in U.S. Pat. No. 5,519,754 and is incorporated by reference herein.

Referring to FIG. 3, the arcuate shaped c-arm 22 is shown having an arcuate shaped wall 24, integrally formed arcuate shaped upper and lower tubular members 26 and 28, respectively and a first and second mounting plate 30 and 32 positioned at first and second opposed ends, 31 and 33 respectively, of c-arm 22. Additionally, a plurality of apertures 34 are formed through wall 24. As shown in FIG. 1, mounting plates 30 and 32 allow an image intensifier 36 and an x-ray head 38 to be mounted to c-arm 22, respectively. In the preferred embodiment, image intensifier 36 is mounted to first mounting plate 30 by four screws and x-ray head 38 is mounted to second mounting plate 32, also by four screws.

Figure 2:
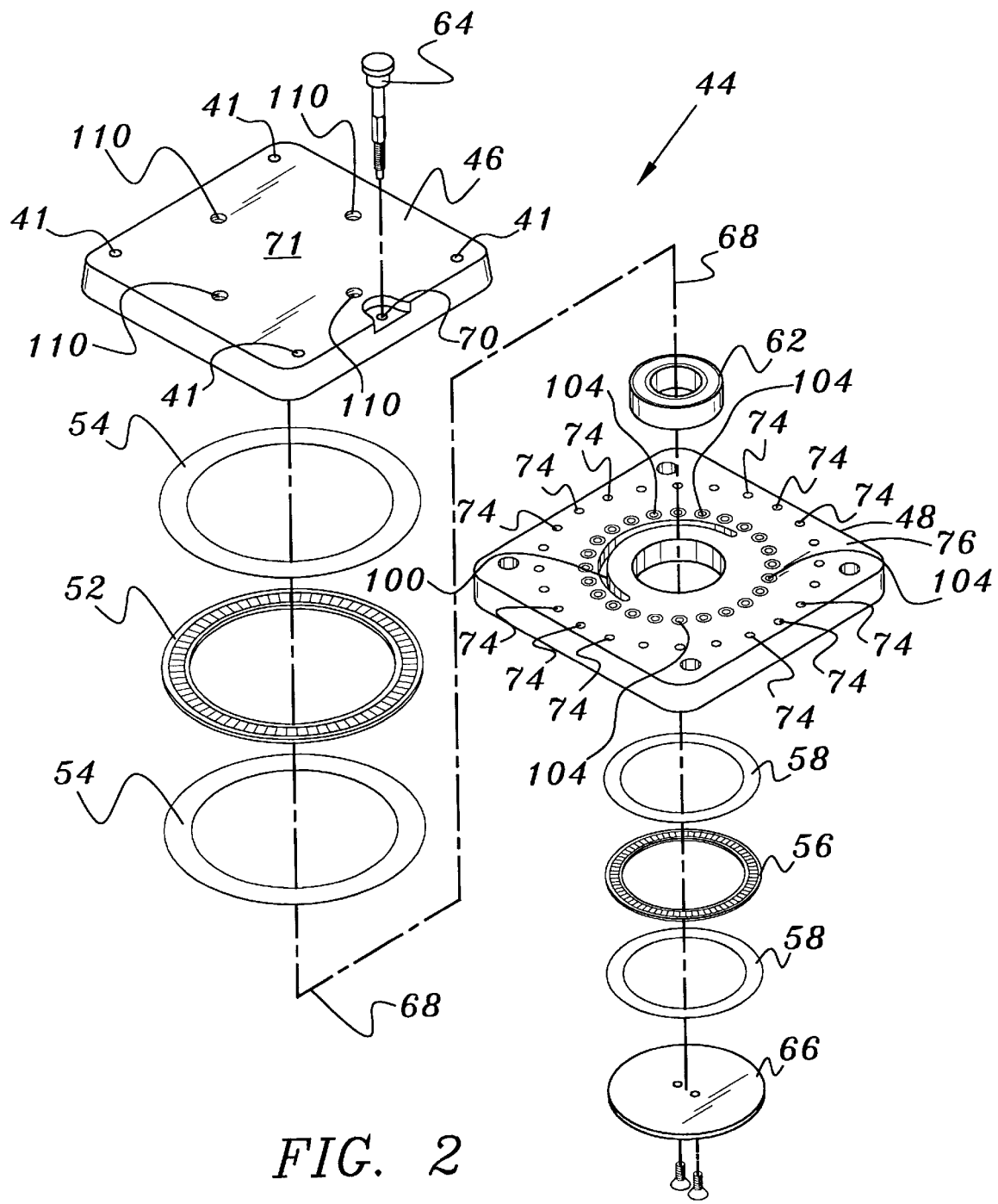
FIG. 2 is an exploded view of a rotation means used to rotate a c-arm of the videofluoroscopy device.

With reference to FIG. 3, c-arm 22 has a first set of mounting holes 40 formed through a middle portion 42 of c-arm 22. As shown in FIG. 1, first set of mounting holes 40 permit four screws to be inserted therethrough for mounting a rotation mechanism 44 to a back side of c-arm 22. As shown in FIG. 2, rotation mechanism 44 has a second set of mounting holes 41 formed therein which are axially aligned with first set 40 for receiving the four mounting screws inserting through c-arm 22. As shown in FIG. 4, rotation mechanism 44 has a third set of mounting holes 50 formed therein which are axially aligned with mounting holes formed in a mounting block (not shown) for receiving screws inserting through the mounting block thereby affixing rotation means 44 to videofluoroscopy device 10 and thereby permitting c-arm 22 to communicate with worm screw 20.

With continuing reference to FIG. 4, rotation mechanism 44 is shown in an partially exploded view. Rotation mechanism 44 is generally square-shaped and has a moveable front frame 46 and a fixed back frame 48. As shown in FIG. 2 (fully exploded view), rotation mechanism 44 has a first set of circular thrust bearings 52, surrounded by a first set of circular washers 54, a second set of circular thrust bearings 56, surrounded by a second set of circular washers 58, a tubular center shaft 60 (see FIG. 4), a third set of axial bearings 62 surrounding center shaft 60, a pin locking mechanism 64, a circular plate 66 for enclosing second set of thrust bearings 56 and second set of washers 58 within back frame 48, a 180 degree stop mechanism, a 15 degree stop mechanism and a horizontal axis 68, perpendicular to vertical axis 16 when rotation mechanism 44 is mounted to videofluoroscopy device 10. Circular plate 66 mounts against a back face 78 (see FIG. 4) of back frame 48 by a pair of screws. A cavity (not shown) formed in back frame back face 78 receives second thrust bearings 56 and second set of washers 58 which circular plate 66 encloses therewithin such that a top surface of circular plate 66 is flush with back frame back face 78, as shown in FIG. 4. Center shaft 60 mounts within a bore (see FIG. 5) formed in a back face 80 of front frame 46, protruding therefrom along horizontal axis 68 and has a set of fourth mounting holes 82 formed in a top portion 84 of center shaft 60 for receiving the pair of screws that lock circular plate 66 to rotation mechanism 44, as seen in FIG. 4. Axial bearing 62 permits front frame 46 to rotate about center shaft 60 while circular plate 66 stays locked in position to center shaft 60. Since circular plate 66 stays stationary with center shaft 60 while front frame 46 rotates, second set of thrust bearings 56 are provided to diffract any friction caused between circular plate 66 and back frame 48. Likewise, first set of thrust bearings 52 are provided to diffract friction caused between front frame 46 and back frame 48 when front frame 46 is rotated. As shown in FIG. 4, first set of thrust bearings 52 and first set of washers 54 are positioned in a groove (not shown) formed in front frame back face 80.

Referring to FIG. 2, pin locking mechanism 64 is a spring loaded pin insertable through an aperture 70 formed through a front face 71 in front frame 46. A tip portion 72 (see FIG. 5) of locking mechanism 64 is received by one of a plurality of detente bores 74 formed in back frame front face 76 at fifteen degree angles (see FIG. 2). Accordingly, locking mechanism 64 permits c-arm 22 to be moved in 15 degree angles, 90 degrees in each direction, for a total rotation of 180 degrees.

To assist in locking down c-arm 22 in successive 15 degree angles, the 15 degree stop mechanism is employed. The 15 degree stop mechanism has a series of stop bores 104, as seen in FIGS. 2 and 5, for receiving one of four spring loaded balls 106 as seen in FIGS. 4 and 5. In the preferred embodiment stop bores 104 are concave plugs inserted within a series of apertures 108 formed in back frame 48 whose number are proportional to the number of detente bores 74 used to receive pin locking mechanism tip portion 72. As seen in FIG. 2, detente bores 74 are spaced near an outer edge of back frame 76 whereas stop bores 104 are spaced between detente bores 74 and horizontal axis 68. The four spring loaded balls 106 insert through four threaded apertures 110 formed through front frame 46.

The 180 degree stop mechanism ensures that c-arm 22 does not rotate further then a total of 180 degrees, 90 degrees in each direction from a line perpendicular to vertical axis 16. As shown in FIG. 2, an arcuate c-shaped channel 100 is formed in back frame front face 76. As shown in FIG. 4, a stop pin 102 inserts within front frame back face 80. As front frame 46 is rotated, stop pin 102 reaches a limit of 90 degrees in each direction from a line perpendicular to vertical axis 16, thereby providing a total turn ratio of 180 degrees.

As illustrated in FIG. 1, with an x axis being perpendicular to vertical axis 16 and a y axis being parallel to vertical axis 16, c-arm 22 is shown at a 15 degree angle with x-ray head 38 positioned in the negative x/positive y quadrant, and the broken line illustration of c-arm 22 showing a 45 degree angle with x-ray head 38 positioned in the positive x/positive y quadrant.

With continuing reference to FIG. 1, is it shown that a video camera 86 mounts upon a top portion 88 of x-ray head 38. In the preferred embodiment, a three chip CCD camera is used. A video signal output of video camera 86 and a signal output of an x-ray head controller (a unit capable of interpreting x-ray image data and outputting that data as a video signal output) are coupled to a video monitor 90 (see FIG. 6) and a video tape recorder (not shown) through a black box (also not shown) containing an electrical circuit capable of outputting two simultaneous images, one smaller image laid over a larger image, to video monitor 90 and the video tape recorder. A printer (also not shown) may be coupled to the system permitting an operator to print a still shot at any particular moment during the videofluoroscopy procedure.

Figure 6:
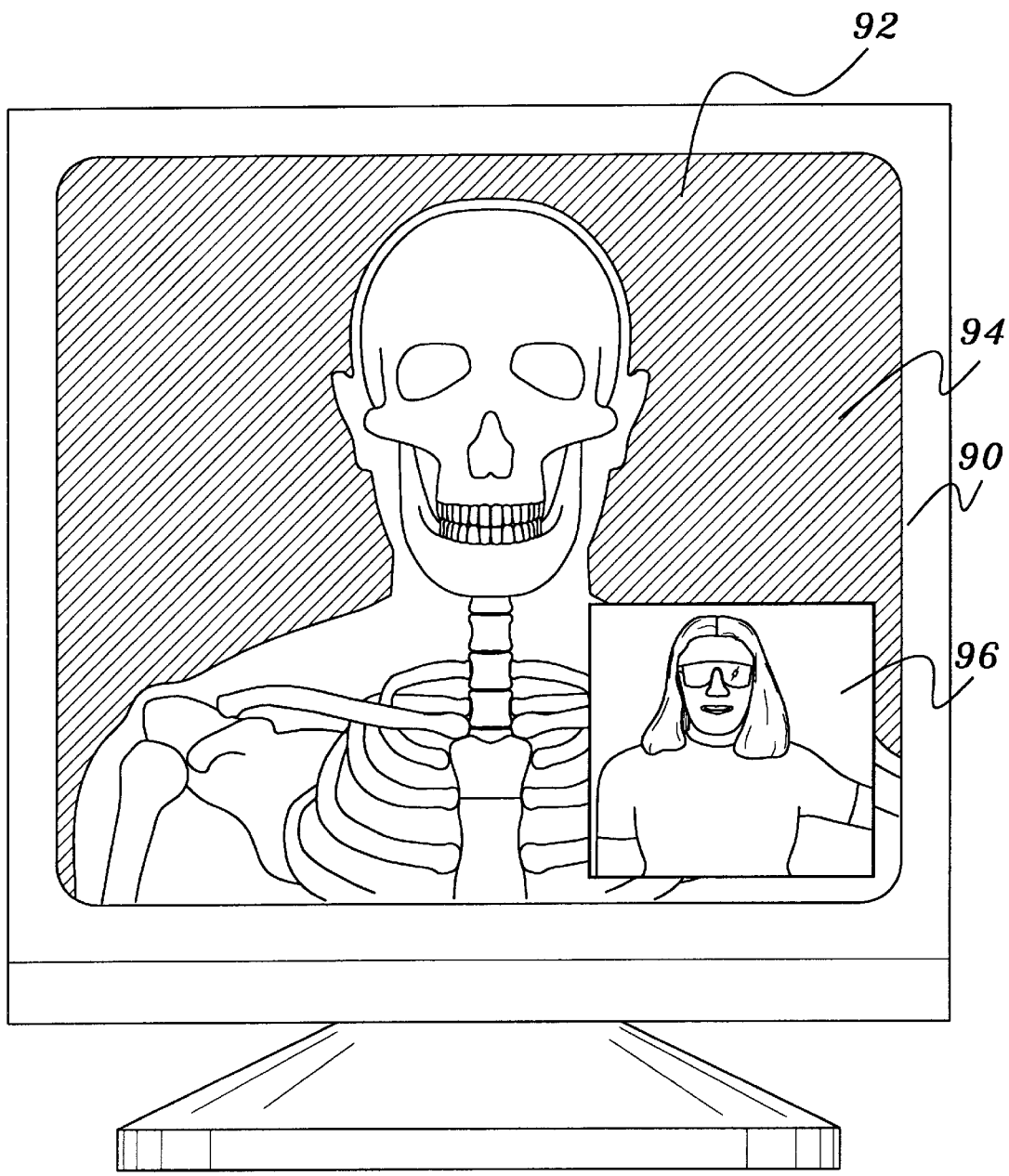
FIG. 6 is an illustration of a PIP motion x-ray image capable of being produced by the system and method of the present invention.

Referring to FIG. 6, a PIP x-ray image 92 is shown. It is understood that FIG. 6 represents a "full-screen" real time x-ray image 94 having a smaller real time external patient image 96, corresponding to the portion of the body being x-rayed, in one of the four corners of full-screen image 94.

Figure 7:
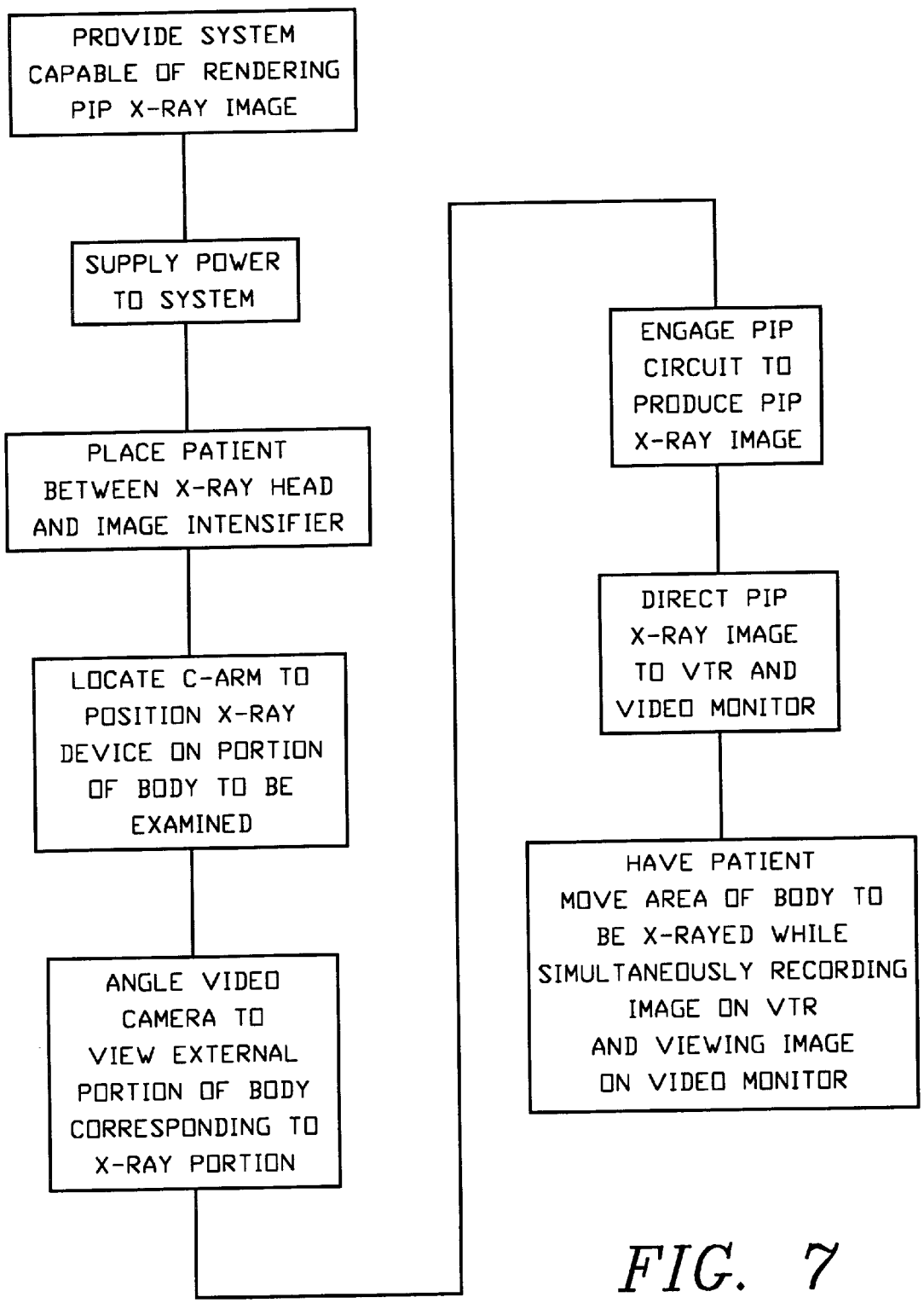
FIG. 7 is a block diagram of the steps carried out in the method of the present invention.

To render the PIP real time x-ray image, a series of steps are carried out which represent the novel method of the present invention. Referring to FIG. 7, the steps of the novel method are set out. First, a system capable of rendering the PIP real time x-ray image is provided. The system includes at least videofluoroscopy device 10, video camera 86, the x-ray controller, video monitor 90 and the PIP circuit enclosed within the black box. Optionally, the video tape recorder and printer can be added to the system if the operator desires to record the procedure or print still shots. Secondly, power is supplied to the system. Thirdly, the patient is placed between x-ray head 38 and image intensifier 36. Fourthly, c-arm 22 is located such that the x-ray device (comprising x-ray head 38 and image intensifier 36) is positioned on a portion of the body of the patient to be examined. Fifthly, video camera 86 is angled at the patient to view the external portion of the patient body corresponding to the portion to be x-rayed. Sixthly, the PIP circuitry is engaged and directed to video monitor 90 and the video tape recorder and printer if being used. Finally, the patient is asked to flex or move the portion of the body to be diagnosed so that the PIP real time motion image is rendered on the monitoring and/or recording equipment.

The PIP circuit enclosed within the black box provides a means for moving the smaller external image to any of the four corners of the screen. Further, there are no limitations providing that the external image be the smaller image. In the preferred method, the x-ray image is the larger full-screen image while the external view of the patient is the smaller image in the box at one of the four corners. To impart consistency to the PIP real time motion x-ray image procedure, a protocol can be established from which the operators of the system can follow. For instance, in the preferred method, the following protocol is practiced. First, before proceeding with any examination, a patient ID picture is rendered. In this step, the patient to be examined stands in front of the video camera with an erasable board having the patient's name, the date of the procedure and the name of the examining doctor. Next the patient is placed between the x-ray head and image intensifier mounted on the c-arm of the videofluoroscopy device. If lateral nodding is to be checked, the aiming mechanism of the x-ray head is set one inch below the earlobe with the patient positioned sideways facing the videofluoroscopy device; the external camera view is placed in the lower left corner. If lateral flexion and extension is to be checked, the aiming mechanism is set at vertebra C4 with the patient positioned sideways facing the videofluoroscopy device; the external camera view is placed in the lower left corner. If oblique flexion and extension is to be checked, the aiming mechanism is set at vertebra C4 (or slightly lower) with the patient positioned sideways facing the videofluoroscopy device; the external camera view is placed in the lower left corner. If AP cervical lateral flexion is to be checked, the aiming mechanism is set at vertebra C4 (or slightly lower) with the patient facing the video camera; the external camera view is placed in the lower right corner. If rotation is to be checked, the aiming mechanism is set between the lips with the patient facing the video camera; the external camera view is placed in the lower right corner. If AP open mouth (lateral flexion) is to be checked, the aiming mechanism is set between the chin with the patient facing the video camera; the external camera view is placed in the lower right corner.

The x-ray device used on videofluoroscopy device 10 also includes a collimation device (a unit used to reduce scatter radiation which helps to sharpen the image). As seen in FIG. 1, controls 98 for the collimation device are included on x-ray head 38. The preferred protocols used, described herein above, also include preferred settings for collimation.

The system of the present invention can also include a microphone which permits the operator of the system to hear any comments made by the patient as well as listen for any noises associated with the movement of a given muscle, joint or bone.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A videofluoroscopy system for providing a picture-in-a-picture real time x-ray image, the videofluoroscopy system comprising:

a) a videofluoroscopy device having a vertical housing defining a vertical channel and a vertical axis, an arm-member having a back side, an x-ray device having a signal output, vertical movement means enclosed within the vertical channel for moving the arm-member along the vertical axis, rotation means mounted along the back side of the arm-member for rotating the arm-member from the vertical axis and a mounting block positioned between the vertical movement means and the rotation means providing communication therebetween, b) a video camera mounted upon the arm-member, proximal to the x-ray device and having a video signal output, c) a controller having at least one input and at least one output, the at least one input receiving the x-ray device signal output, the controller converting the x-ray device signal to a video signal output and directing it to the at least one controller output, d) an electrical circuit having at least two video signal inputs and at least one video signal output, one of the at least two video signal inputs receiving the video camera video signal output and another one of the at least two video signal inputs receiving the controller video signal output, the electrical circuit capable of combining the two video signals into a single image video signal having a first smaller image overlaid a second larger image, the single image video signal directed to the at least one video signal output of the electrical circuit, the single image video signal representing the picture-in-a-picture real time x-ray image, e) a monitor for viewing the picture-in-a-picture real time x-ray image, and f) power means coupled to the system for supplying electrical power thereto.

2. The system of claim 1 further comprising, a video tape recorder coupled to the at least one video signal output of the electrical circuit for recording the picture-in-a-picture real time x-ray image on video tape.

3. The system of claim 1, wherein the arm-member is a c-arm having an arcuate shaped wall, integrally formed upper and lower tubular portions, first and second opposed ends and first and second mounting plates respectively attached to the first and second opposed ends.

4. The system of claim 3, wherein the x-ray device comprises an image intensifier and an x-ray head, the image intensifier mounted on the first c-arm mounting plate and the x-ray head mounted on the second c-arm mounting plate.

5. The system of claim 1, wherein the vertical movement means comprises:

a) a pair of guide rails positioned in the vertical channel along the vertical axis, b) a worm screw positioned along the vertical axis between the pair of guide rails, and c) a motor mounted in a bottom portion of the vertical housing communicating with the worm screw.

6. The system of claim 1, wherein the rotation means comprises:

a) a horizontal axis intersecting the videofluoroscopy device vertical axis along a line moving from a front side to a back side of the videofluoroscopy device, the horizontal axis moving vertically, proportional to any vertical movement of the arm-member, b) a generally square-shaped front and back frame, each having front and back faces, the front frame front face mounting to the arm-member back side, the back frame back face attached to the mounting block, the front frame back face mounting to the back frame front face, the back frame being in a fixed position, the front frame rotatable around the horizontal axis, c) a first set of circular thrust bearings surrounded by a first pair of circular washers and positioned in a groove formed in the front frame back face, d) a second set of circular thrust bearings surrounded by a second pair of circular washers and positioned in a cavity formed in the back frame back face, e) a circular plate member insertable within the cavity covering the second set of circular thrust bearings and the second pair of circular washers, the circular plate member having a pair of apertures formed therethrough for receiving a pair of screws, the screws mounting the circular plate member to the rotation means, f) a center shaft mounted in the front frame back face and axially aligned with the horizontal axis, the center shaft having a pair of receiving bores formed in a top portion engaging the pair of circular plate member screws, g) an axial set of bearings surrounding the center shaft, and h) locking means for securing the front frame to the back frame.

7. The system of claim 6, wherein the locking means is a spring loaded pin having a tip portion insertable through a lock aperture formed through the front frame, the tip portion engaging one of a plurality of detente bores formed in the back frame front face.

8. The system of claim 7, wherein the detente bores are spaced at fifteen degree angles.

9. The system of claim 6, further comprising:

a) a plurality of stop bores formed in the back frame front face, b) four spring loaded balls inserted within four threaded apertures formed through the front plate, the four spring loaded balls spaced at ninety degree angles from one another and protruding slightly from the front frame back face, each ball engaging one of four of the plurality of stop bores, c) a stop pin inserted within a stop pin aperture formed in the front frame back face, and d) an arcuate c-shaped channel formed in the back frame front face for communicating with the stop pin to limit the distance that the front face can rotate around the horizontal axis.

10. The system of claim 9, wherein the front face can rotate 180 degrees about the horizontal axis.

11. The system of claim 1, wherein the power means is an AC power source.

12. The system of claim 1, wherein the power means is a DC power source.

13. A videofluoroscopy system for providing a picture-in-a-picture real time x-ray image, the videofluoroscopy system comprising:

a) a videofluoroscopy device comprising:

(i) a vertical housing having a bottom portion and defining a vertical channel and vertical axis, (ii) a c-arm having an arcuate shaped wall, integrally formed upper and lower tubular portions, first and second opposed ends, first and second mounting plates respectively attached to the first and second opposed ends and a back side, (iii) an image intensifier mounted on the first c-arm mounting plate, (iv) an x-ray head mounted on the second c-arm mounting plate, (v) the image intensifier and x-ray head defining an x-ray device, the x-ray device having a signal output, (vi) a pair of guide rails positioned in the vertical channel along the vertical axis, (vii) a worm screw positioned along the vertical axis between the pair of guide rails, (viii) a motor mounted in the vertical housing bottom portion communicating with the worm screw, (ix) rotation means mounted along the back side of the arm-member for rotating the arm-member from the vertical axis, and (x) a mounting block positioned between the vertical movement means and the guide rails and worm screw providing communication therebetween, b) a video camera mounted upon the x-ray head and having a video signal output, c) a controller having an input and an output, the controller input receiving the x-ray device signal output, the controller converting the x-ray device signal to a video signal and directing it to the controller output, d) an electrical circuit having two video signal inputs and a video signal output, one of the video signal inputs receiving the video camera video signal output and the other video signal input receiving the controller video signal output, the electrical circuit capable of combining the two video signals into a single image video signal having a first smaller image overlaid a second larger image, the single image video signal directed to the video signal output of the electrical circuit, the single image video signal representing the picture-in-a-picture real time x-ray image, e) a monitor for viewing the picture-in-a-picture real time x-ray image, and f) power means coupled to the system for supplying electrical power thereto.

14. The system of claim 13, wherein the rotation means comprises:

a) a horizontal axis intersecting the videofluoroscopy device vertical axis along a line moving from a front side to a back side of the videofluoroscopy device, the horizontal axis moving vertically, proportional to any vertical movement of the c-arm, b) a generally square-shaped front and back frame, each having front and back faces, the front frame front face mounting to the c-arm back side, the back frame back face attached to the mounting block, the front frame back face mounting to the back frame front face, the back frame being in a fixed position, the front frame rotatable about the horizontal axis, c) a first set of circular thrust bearings surrounded by a first pair of circular washers and positioned in a groove formed in the front frame back face, d) a second set of circular thrust bearings surrounded by a second pair of circular washers and positioned in a cavity formed in the back frame back face, e) a circular plate member insertable within the cavity covering the second set of circular thrust bearings and the second pair of circular washers, the circular plate member having a pair of apertures formed therethrough for receiving a pair of screws, the screws mounting the circular plate member to the rotation means, f) a center shaft mounted in the front frame back face and axially aligned with the horizontal axis, the center shaft having a pair of receiving bores formed in a top portion engaging the pair of circular plate member screws, g) an axial set of bearings surrounding the center shaft, and h) locking means for securing the front frame to the back frame.

15. The system of claim 14, wherein the locking means is a spring loaded pin having a tip portion insertable through a lock aperture formed through the front frame, the tip portion engaging one of a plurality of detente bores formed in the back frame front face.

16. The system of claim 15, wherein the detente bores are spaced at fifteen degree angles.

17. The system of claim 13, further comprising:

a) a plurality of stop bores formed in the back frame front face, b) four spring loaded balls inserted within four threaded apertures formed through the front plate, the four spring loaded balls spaced at ninety degree angles from one another and protruding slightly from the front frame back face, each ball engaging one of four of the plurality of stop bores, c) a stop pin inserted within a stop pin aperture formed in the front frame back face, and d) an arcuate c-shaped channel formed in the back frame front face for communicating with the stop pin to limit the distance that the front face can rotate around the horizontal axis to 180 degrees.

18. The system of claim 13, wherein the first smaller image is a real time video of an external view of a patient positioned in front of the video camera and the second larger image is a real time video x-ray image of an internal body portion of the patient corresponding to the external view.

19. A method of producing a picture-in-a-picture real time x-ray image, the steps comprising:

a) providing a videofluoroscopy device having a vertical housing defining a vertical channel and a vertical axis, an arm-member having a back side, vertical movement means enclosed within the vertical channel for moving the arm-member along the vertical axis, mounting means positioned between the vertical movement means and the arm-member back side providing communication therebetween, an x-ray device mounted upon the arm-member and having a signal output, an x-ray controller having an input and an output, the controller input receiving the x-ray device signal output, the controller converting the x-ray device signal to a video signal and directing it to the controller output, b) mounting a video camera upon the arm-member, proximal to the x-ray device, the video camera having a video signal output, c) providing an electrical circuit having at least two video signal inputs and at least one video signal output, the electrical circuit capable of combining two inputted video signals into a single image video signal having a first smaller image overlaid a second larger image, the electrical circuit capable of directing the single image video signal to the at least one video signal output, d) coupling one of the electrical circuit at least two video signal inputs to the video camera video signal output, e) coupling another one of the controller at least two video signal inputs to the controller video signal output, f) providing a video monitor having a video signal input, g) coupling the video monitor video signal input to the electrical circuit at least one video signal output, h) supplying electrical current to the videofluoroscopy device, video camera, electrical circuit and video monitor, i) positioning a patient in front of the x-ray device, j) locating the arm-member to position the x-ray device on a body portion of the patient to be examined, k) angling the video camera to view an external body portion of the patient corresponding to the body portion to be x-rayed, and l) engaging the electrical circuit to produce the single video image having the first smaller image overlaid the second larger image.

20. The method of claim 19, further comprising the steps of:

a) providing a video tape recorder having a video signal input, b) coupling the video tape recorder video signal input to the electrical circuit at least one video signal output, and c) recording the single video image of the first smaller image overlaid the second larger image on video tape.

* * * * *